United States Patent
Li et al.

(10) Patent No.: US 8,846,853 B2
(45) Date of Patent: Sep. 30, 2014

(54) POLYCONDENSATION OF LACTIC ACID FOR MEDICAL BIODEGRADABLE POLYLACTIC ACID CATALYZED BY CREATININE

(75) Inventors: Hong Li, Jiangsu (CN); Quanxing Zhang, Jiangsu (CN); Wei Jiang, Jiangsu (CN); Wei Huang, Jiangsu (CN); Bingcai Pan, Jiangsu (CN)

(73) Assignee: Nanjing University, Nanjing, Jiangsu (CN)

( * ) Notice: Subject to any disclaimer, the term of this patent is extended or adjusted under 35 U.S.C. 154(b) by 72 days.

(21) Appl. No.: 13/511,311

(22) PCT Filed: Nov. 3, 2011

(86) PCT No.: PCT/CN2011/081723
§ 371 (c)(1),
(2), (4) Date: Oct. 2, 2012

(87) PCT Pub. No.: WO2012/122807
PCT Pub. Date: Sep. 20, 2012

(65) Prior Publication Data
US 2013/0116400 A1     May 9, 2013

(51) Int. Cl.
*C08G 63/08* (2006.01)
*A61K 47/32* (2006.01)
*C08G 63/82* (2006.01)

(52) U.S. Cl.
CPC .............. *C08G 63/823* (2013.01); *A61K 47/32* (2013.01); *C08G 63/08* (2013.01)
USPC ............ 528/361; 528/271; 502/167; 502/200

(58) Field of Classification Search
CPC ....... C08G 63/823; C08G 63/08; A61K 47/34
USPC ........................ 528/271, 361; 502/167, 200
See application file for complete search history.

(56) References Cited

U.S. PATENT DOCUMENTS

2011/0003949 A1*   1/2011   Hedrick et al. .................. 526/75
2011/0263811 A1*   10/2011   Sawai et al. .................... 528/272

OTHER PUBLICATIONS

Wang et al, "Ring Opening Polymerization of L-Lactide Initiated by Creatinine", Biomaterials, 2004, vol. 25, pp. 5797-5801.*

* cited by examiner

*Primary Examiner* — Frances Tischler
(74) *Attorney, Agent, or Firm* — Rankin, Hill & Clark LLP

(57) ABSTRACT

A direct polycondensation method for medical biodegradable polylactic acid (PLA). The invention uses commercialized creatinine (a type of biomaterial organic guanidine compounds—the arginine metabolite creatinine in human body) as the catalyst and industrial lactic acid (mass content 85-90%, aqueous solution) as the monomer to synthesize the PLA in terms of second polycondensation without solvent. Instead of tin catalysts having cytotoxicity, the catalyst used in the invention has high biocompatibility and biosafety. The synthesized PLA does not contain any metal and other toxic components; therefore, it can be used as the carrier for targeting drugs and controlled release drugs. The green catalyst and green processing method (no solvent applied and no toxic products produced) are used to synthesize the green biodegradable PLA with high biosafety. The molecular weight distribution for all synthesized products is narrow and the molecular weight is controllable within $1.5\text{-}3.0\times10^4$.

2 Claims, No Drawings

POLYCONDENSATION OF LACTIC ACID FOR MEDICAL BIODEGRADABLE POLYLACTIC ACID CATALYZED BY CREATININE

FIELD OF THE INVENTION

The present invention pertains to the category of medical biodegradable materials, more particularly it relates to a polycondensation method for high biosafety of polylactic acid (PLA) using biomaterial (nontoxic organic material produced in human metabolism) creatinine catalyst.

BACKGROUND OF THE INVENTION

In recent years, along with the rapid development of pharmacological and biomedical science, medical biodegradable materials having excellent biocompatibility and biosafety are increasingly demanded internationally and domestically. The biodegradable PLA has been significantly applied in pharmacological and biomedical science, for example, it is used as the carrier for targeting drugs and controlled release drugs, hard tissue repair material and supporting material for biologically active species in biomedical engineering. By using PLA as the drug carrier, the medical effect can be largely improved, and the dosage and drug's side effects can be reduced. When PLA is used as the drug carrier, the polymer with the weight average molecular weight (Mw) $1.5 \times 10^4 \sim 3.0 \times 10^4$ is generally used (Zhao, Y.; Wang, Z.; Yang, F. J. Appl. Polym. Sci., 2005, 97, 195-200). However, such polymer should not contain any toxic metal and other toxic components. Currently, commercial PLA is produced mainly by the following two methods: 1. It is synthesized by using stannous octoate to catalyze lactide by ring-opening polymerization; and 2. It is synthesized by using stannous chloride to catalyze lactic acid by direct polycondensation. Although these two methods can be used to synthesize the required polymer, the catalyst tin salt cannot be completely removed from the polymer after polymerization reaction. Many researches have been conducted by foreign and Chinese scholars to prove that stannous octoate and stannous chloride have cytotoxicity. Consequently, scientists around the world start to question the safety of PLA that is synthesized by using stannous octoate and stannous chloride as the catalyst and which is used as the pharmaceutical carrier. The most important problem raised by worldwide biomedical material scientists to be solved is to use the high-effective and nontoxic catalyst to synthesize the medical PLA. At present, there are two methods using non-metal catalysts to synthesize the biodegradable PLA in terms of ring-opening polymerization: 1. Two-component catalysis. This method is developed by American scholar J. L. Hedrick et al. The principle is that a strong phosphine-amine nucleophilic reagent (e.g. triphenylphosphine, 4-dimethylaminopyridine, etc.) is used as the catalyst and alcohol (e.g. pyrenyl butanol, methanol, benzyl alcohol, etc.) as the initiator to prepare the PLA biodegradable polymer in terms of the ring-opening polymerization; and 2. Nontoxic and non-metal organic guanidine is used to synthesize the PLA. This method is firstly developed by Chinese scholar Li Hong (Distinguished Professor of School of the Environment, Nanjing University). The non-toxic and biomimetic organic guanidine (creatinine, creatine, glycocyamine, six alkyl acid guanidine, etc.) without metal and biomaterial is used as the mono-component catalyst to trigger the lactide activity to synthesize the PLA in terms of the controlled ring-opening polymerization. The direct polycondensation method used to synthesize the PLA is the one developed by Japanese scholar Y. Kimura by using stannous chloride to catalyze lactic acid. The advantage of such method is that lactic acid is directly used as the monomer (the ring-opening polymerization needs high purity of lactide made by lactic acid cyclic dimer as the monomer) and high-purity of monomer is not required, therefore, PLA production costs are largely reduced and it is possible for industrialization.

SUMMARY OF THE INVENTION

In view of the above-described problems, it is one objective of the invention to overcome the potential safety problem of PLA as pharmaceutical carrier synthesized in terms of polycondensation by the catalyst stannous chloride that cannot be completely removed from the polymer by providing a direct polycondensation method for medical biodegradable polylactic acid with high biosafety using nontoxic organic guanidine compounds without metal biomaterials as the catalyst.

In the present invention, a new polycondensation method for the high biosafety of PLA using the nontoxic organic guanidine compounds (the arginine metabolite creatinine in human body) without metal biomaterials as the catalyst and the lactic acid (85-90% aqueous solution) as the monomer is firstly developed.

The preferred IUPAC name for the nontoxic organic guanidine compounds without metal biomaterials—creatinine used in the invention is 2-amino-1-methyl-2-imidazolin-4-one, English name creatinine (CR) and the molecular structure is:

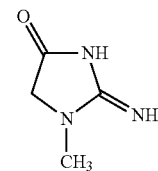

Creatinine (CR)

The direct polycondensation method for medical biodegradable polylactic acid using creatinine catalyzed lactic acid provided by the invention uses the biomaterial organic guanidine compounds (the arginine metabolite creatinine in human body) as the catalyst and the lactic acid (85-90% aqueous solution) as the monomer to synthesize the high biosafety of PLA in terms of the polycondensation method, specifically, it includes:

Synthetic Route:

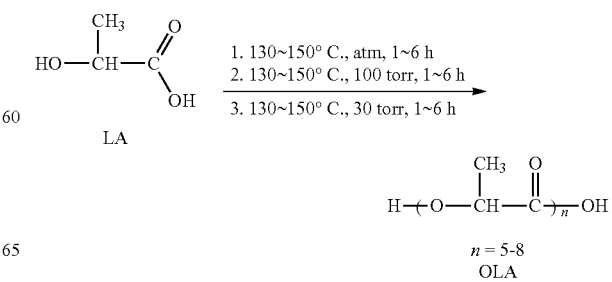

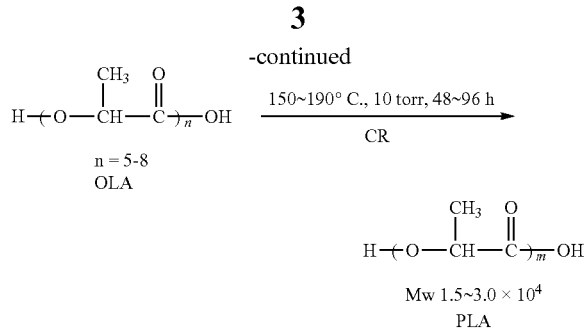

$$\text{n = 5-8}$$
OLA $$\xrightarrow{150\sim190°\text{C., 10 torr, 48}\sim96\text{ h}}{CR}$$

$$H\!-\!\!\!(\!O\!-\!\!CH(CH_3)\!-\!C(O)\!)_m\!\!-\!OH$$

Mw $1.5\sim3.0 \times 10^4$
PLA

Synthetic Steps:

Step 1: Synthesis of Oligomers of Lactic Acid (OLA)

Use industrial lactic acid (LA, mass content 85-90%, aqueous solution) as the monomer to firstly synthesize the OLA with number average molecular weight (Mn) of 400-600. Synthesis conditions: add lactic acid in a reaction vessel and repeatedly vacuumize the vessel and fill in the argon gas for three times. Heat under argon atmosphere and normal pressure until the temperature reaches 130-150° C. and dehydrate for 1-6 hrs. Reduce the pressure of the reaction vessel to 100 Torr and further dehydrate for 1-6 hrs under the temperature of 130-150° C. Afterwards, reduce the pressure of the reaction vessel to 30 Torr and further dehydrate for 1-6 hrs under the temperature of 130-150° C.

Step 2: Synthesis of PLA

Use the OLA obtained from step 1 as the raw material and commercialized creatinine as the catalyst to synthesize the high biosafety of medical PLA under reduced pressure and certain temperature in terms of melt polycondensation. Synthesis conditions: add the catalyst creatinine to the reaction vessel, control the mol ratio of the creatinine to the lactic acid within 1:100-1:1000, reduce the pressure of the reaction vessel to 10 Torr and raise the temperature to 150-190° C. to dehydrate for 48-96 hrs.

The molecular weight of the PLA synthesized by the method provided herein is $1.5\sim3.0\times10^4$ and the polydispersity index (PDI) is 1.70-1.90.

The PLA synthesized by the method provided herein does not contain any metal and other toxic components; therefore, it can be used as the carrier for targeting drugs and controlled release drugs.

Advantages and beneficial effects of the invention are summarized below:
1. The catalyst used in the invention has high biocompatibility and biosafety;
2. The PLA synthesized in the invention does not contain any metal and other toxic components, therefore, it can be used as the carrier for targeting drugs and controlled release drugs;
3. The green catalyst and green processing method (no solvent applied and no toxic products produced) are used in the invention to synthesize green biodegradable PLA with high biosafety;
4. The polymerization reaction is simple and the raw materials required are low in costs, thus it is easy for industrialization.
5. The molecular weight distribution for all synthesized products is narrow and the molecular weight is controllable within $1.5\text{-}3.0\times10^4$.

DETAILED DESCRIPTION OF THE EMBODIMENTS

Example 1

Add 100 g of L-lactic acid (mass content 85-90%) to a reaction vessel and repeatedly vacuumize the vessel and fill in the argon gas for three times. Heat under the argon atmosphere and normal pressure until the temperature reaches 130° C. and dehydrate for 6 hrs. Afterwards, reduce the pressure of the reaction vessel to 100 Torr and further dehydrate for 6 hrs under the temperature of 130° C. After that, reduce the pressure of the reaction vessel to 30 Torr and further dehydrate for 6 hrs under the temperature of 130° C. to obtain the OLA.

Add 204 mg of catalyst creatinine to the reaction vessel, reduce the pressure of the reaction vessel to 10 Torr, and raise the temperature to 165° C. to dehydrate for 48 hrs. After the dehydration stops, cool the reaction vessel to room temperature, use acetone to dissolve the obtained polymer, fill the solution into 0° C. of ethanol, vacuum filtration of the solution, and dry the obtained solid under the temperature of 50° C. and vacuum condition for 36 hrs to obtain the white solid, i.e. high biosafety of medical PLA with yield at 85.0% and polymer's molecular weight at $2.0\times10_4$, PDI 1.70.

Example 2

Add 100 g of D, L-lactic acid (mass content 85-90%) to a reaction vessel and repeatedly vacuumize the vessel and fill in the argon gas for three times. Heat under the argon atmosphere and normal pressure until the temperature reaches 130° C. and dehydrate for 6 hrs. Afterwards, reduce the pressure of the reaction vessel to 100 Torr and further dehydrate for 6 hrs under the temperature of 130° C. After that, reduce the pressure of the reaction vessel to 30 Torr and further dehydrate for 6 hrs under the temperature of 130° C. to obtain the OLA.

Add 204 mg of catalyst creatinine to the reaction vessel, reduce the pressure of the reaction vessel to 10 Torr, and raise the temperature to 150° C. to dehydrate for 96 hrs. After the dehydration stops, cool the reaction vessel to room temperature, use acetone to dissolve the obtained polymer, fill the solution into 0° C. of ethanol, vacuum filtration of the solution, and dry the obtained solid under the temperature of 50° C. and vacuum condition for 36 hrs to obtain the white solid, i.e. high biosafety of medical PLA with yield at 85.9% and polymer's molecular weight at $1.9\times10^4$, PDI 1.72.

Example 3

Add 100 g of L-lactic acid (mass content 85-90%) to a reaction vessel and repeatedly vacuumize the vessel and fill in the argon gas for three times. Heat under the argon atmosphere and normal pressure until the temperature reaches 150° C. and dehydrate for 1 h. Afterwards, reduce the pressure of the reaction vessel to 100 Torr and further dehydrate for 1 h under the temperature of 150° C. After that, reduce the pressure of the reaction vessel to 30 Torr and further dehydrate for 1 h under the temperature of 150° C. to obtain the OLA.

Add 204 mg of catalyst creatinine to the reaction vessel, reduce the pressure of the reaction vessel to 10 Torr, and raise the temperature to 150° C. to dehydrate for 96 hrs. After the dehydration stops, cool the reaction vessel to room temperature, use acetone to dissolve the obtained polymer, fill the solution into 0° C. of ethanol, vacuum filtration of the solu-

Example 4

Add 100 g of D, L-lactic acid (mass content 85-90%) to a reaction vessel and repeatedly vacuumize the vessel and fill in the argon gas for three times. Heat under the argon atmosphere and normal pressure until the temperature reaches 150° C. and dehydrate for 1 h. Afterwards, reduce the pressure of the reaction vessel to 100 Torr and further dehydrate for 1 h under the temperature of 150° C. After that, reduce the pressure of the reaction vessel to 30 Torr and further dehydrate for 1 h under the temperature of 150° C. to obtain the OLA.

Add 204 mg of catalyst creatinine to the reaction vessel, reduce the pressure of the reaction vessel to 10 Torr, and raise the temperature to 150° C. to dehydrate for 96 hrs. After the dehydration stops, cool the reaction vessel to room temperature, use acetone to dissolve the obtained polymer, fill the solution into 0° C. of ethanol, vacuum filtration of the solution, and dry the obtained solid under the temperature of 50° C. and vacuum condition for 36 hrs to obtain the white solid, i.e. high biosafety of medical PLA with yield at 87.2% and polymer's molecular weight at $2.9 \times 10_4$, PDI 1.88.

Example 5

Add 100 g of L-lactic acid (mass content 85-90%) to a reaction vessel and repeatedly vacuumize the vessel and fill in the argon gas for three times. Heat under the argon atmosphere and normal pressure until the temperature reaches 150° C. and dehydrate for 1 h. Afterwards, reduce the pressure of the reaction vessel to 100 Torr and further dehydrate for 1 h under the temperature of 150° C. After that, reduce the pressure of the reaction vessel to 30 Torr and further dehydrate for 1 h under the temperature of 150° C. to obtain the OLA.

Add 204 mg of catalyst creatinine to the reaction vessel, reduce the pressure of the reaction vessel to 10 Torr, and raise the temperature to 180° C. to dehydrate for 48 hrs. After the dehydration stops, cool the reaction vessel to room temperature, use acetone to dissolve the obtained polymer, fill the solution into 0° C. of ethanol, vacuum filtration of the solution, and dry the obtained solid under the temperature of 50° C. and vacuum condition for 36 hrs to obtain the white solid, i.e. high biosafety of medical PLA with yield at 88.3% and polymer's molecular weight at $2.7 \times 10_4$, PDI 1.90.

Example 6

Add 100 g of D, L-lactic acid (mass content 85-90%) to a reaction vessel and repeatedly vacuumize the vessel and fill in the argon gas for three times. Heat under the argon atmosphere and normal pressure until the temperature reaches 150° C. and dehydrate for 1 h. Afterwards, reduce the pressure of the reaction vessel to 100 Torr and further dehydrate for 1 h under the temperature of 150° C. After that, reduce the pressure of the reaction vessel to 30 Torr and further dehydrate for 1 h under the temperature of 150° C. to obtain the OLA.

Add 204 mg of catalyst creatinine to the reaction vessel, reduce the pressure of the reaction vessel to 10 Torr, and raise the temperature to 180° C. to dehydrate for 48 hrs. After the dehydration stops, cool the reaction vessel to room temperature, use acetone to dissolve the obtained polymer, fill the solution into 0° C. of ethanol, vacuum filtration of the solution, and dry the obtained solid under the temperature of 50° C. and vacuum condition for 36 hrs to obtain the white solid, i.e. high biosafety of medical PLA with yield at 87.8% and polymer's molecular weight at $2.9 \times 10_4$, PDI 1.89.

Example 7

Add 100 g of L-lactic acid (mass content 85-90%) to a reaction vessel and repeatedly vacuumize the vessel and fill in the argon gas for three times. Heat under the argon atmosphere and normal pressure until the temperature reaches 140° C. and dehydrate for 3 hrs. Afterwards, reduce the pressure of the reaction vessel to 100 Torr and further dehydrate for 3 hrs under the temperature of 140° C. After that, reduce the pressure of the reaction vessel to 30 Torr and further dehydrate for 3 hrs under the temperature of 140° C. to obtain the OLA.

Add 204 mg of catalyst creatinine to the reaction vessel, reduce the pressure of the reaction vessel to 10 Torr, and raise the temperature to 190° C. to dehydrate for 60 hrs. After the dehydration stops, cool the reaction vessel to room temperature, use acetone to dissolve the obtained polymer, fill the solution into 0° C. of ethanol, vacuum filtration of the solution, and dry the obtained solid under the temperature of 50° C. and vacuum condition for 36 hrs to obtain the white solid, i.e. high biosafety of medical PLA with yield at 83.2% and polymer's molecular weight at $2.4 \times 10_4$, PDI 1.81.

Example 8

Add 100 g of L-lactic acid (mass content 85-90%) to a reaction vessel and repeatedly vacuumize the vessel and fill in the argon gas for three times. Heat under the argon atmosphere and normal pressure until the temperature reaches 150° C. and dehydrate for 3 hrs. Afterwards, reduce the pressure of the reaction vessel to 100 Torr and further dehydrate for 3 hrs under the temperature of 150° C. After that, reduce the pressure of the reaction vessel to 30 Torr and further dehydrate for 3 hrs under the temperature of 150° C. to obtain the OLA.

Add 107 mg of catalyst creatinine to the reaction vessel, reduce the pressure of the reaction vessel to 10 Torr, and raise the temperature to 180° C. to dehydrate for 72 hrs. After the dehydration stops, cool the reaction vessel to room temperature, use acetone to dissolve the obtained polymer, fill the solution into 0° C. of ethanol, vacuum filtration of the solution, and dry the obtained solid under the temperature of 50° C. and vacuum condition for 36 hrs to obtain the white solid, i.e. high biosafety of medical PLA with yield at 88.1% and polymer's molecular weight at $2.6 \times 10_4$, PDI 1.79.

Example 9

Add 100 g of L-lactic acid (mass content 85-90%) to a reaction vessel and repeatedly vacuumize the vessel and fill in the argon gas for three times. Heat under the argon atmosphere and normal pressure until the temperature reaches 150° C. and dehydrate for 1 h. Afterwards, reduce the pressure of the reaction vessel to 100 Torr and further dehydrate for 1 h under the temperature of 150° C. After that, reduce the pressure of the reaction vessel to 30 Torr and further dehydrate for 1 h under the temperature of 150° C. to obtain the OLA.

Add 534 mg of catalyst creatinine to the reaction vessel, reduce the pressure of the reaction vessel to 10 Torr, and raise the temperature to 150° C. to dehydrate for 72 hrs. After the dehydration stops, cool the reaction vessel to room temperature, use acetone to dissolve the obtained polymer, fill the solution into 0° C. of ethanol, vacuum filtration of the solution, and dry the obtained solid under the temperature of 50° C. and vacuum condition for 36 hrs to obtain the white solid, i.e. high biosafety of medical PLA with yield at 83.2% and polymer's molecular weight at $2.2 \times 10_4$, PDI 1.87.

Example 10

Add 100 g of D, L-lactic acid (mass content 85-90%) to a reaction vessel and repeatedly vacuumize the vessel and fill in the argon gas for three times. Heat under the argon atmosphere and normal pressure until the temperature reaches 130° C. and dehydrate for 3 hrs. Afterwards, reduce the pressure of the reaction vessel to 100 Torr and further dehydrate for 3 hrs under the temperature of 130° C. After that, reduce the pressure of the reaction vessel to 30 Torr and further dehydrate for 3 hrs under the temperature of 130° C. to obtain the OLA.

Add 1068 mg of catalyst creatinine to the reaction vessel, reduce the pressure of the reaction vessel to 10 Torr, and raise the temperature to 160° C. to dehydrate for 72 hrs. After the dehydration stops, cool the reaction vessel to room temperature, use acetone to dissolve the obtained polymer, fill the solution into 0° C. of ethanol, vacuum filtration of the solution, and dry the obtained solid under the temperature of 50° C. and vacuum condition for 36 hrs to obtain the white solid, i.e. high biosafety of medical PLA with yield at 84.8% and polymer's molecular weight at $1.8 \times 10_4$, PDI 1.82.

The invention claimed is:

1. A method of polycondensing polylactic acid comprising:
   a. subjecting a reaction vessel containing an 85-90 mass % aqueous solution of lactic acid to a vacuum and filling the vessel with argon,
   b. repeating step (a) three times,
   c. with argon remaining in the vessel, heating to 130-150° C. to dehydrate the lactic acid for 1-6 hours,
   d. reducing the vessel pressure to 100 Torr to dehydrate at 130-150° C. for 1-6 hours,
   e. reducing the vessel pressure to 30 Torr to dehydrate at 130-150° C. for 1-6 hours to form n moles of oligomers of lactic acid having 5-8 lactic acid repeat units,
   f. adding 0.001 n to 0.01 n moles of creatinine to the reaction vessel, and
   g. reducing the vessel pressure to 10 Torr and heating to 150-190° C. for 48-96 hours to produce the polylactic acid.

2. The method of claim 1, wherein the polylactic acid has a molecular weight of 15,000 to 30,000 and a polydispersity index of 1.70-1.90.

* * * * *